United States Patent [19]
Metcalfe

[11] Patent Number: 5,133,662
[45] Date of Patent: Jul. 28, 1992

[54] TOOTH IMPLANT DEVICE

[76] Inventor: Edwin R. Metcalfe, 503 Armstrong, Apartment 1, Kansas City, Kans. 60601

[21] Appl. No.: 753,978

[22] Filed: Sep. 3, 1991

[51] Int. Cl.⁵ ............................................. A61C 8/00
[52] U.S. Cl. ........................................ 433/169; 433/172; 433/173; 433/176; 433/193
[58] Field of Search ............... 433/169, 172, 173, 174, 433/175, 176, 193, 194

[56] References Cited
U.S. PATENT DOCUMENTS

| | | | |
|---|---|---|---|
| 2,303,874 | 12/1942 | Brown | 433/194 |
| 3,618,212 | 11/1971 | Weissman | 433/174 |
| 3,977,081 | 8/1976 | Zambelli et al. | 433/176 |
| 3,991,472 | 11/1976 | Lukesch | 433/169 |
| 4,416,629 | 11/1983 | Mozsary et al. | 433/173 |
| 4,568,285 | 2/1986 | Chiaramonte et al. | 433/173 |
| 4,746,293 | 5/1988 | Lundgren et al. | 433/169 |
| 4,850,869 | 7/1989 | Steinfort et al. | 433/193 |
| 4,881,897 | 11/1989 | Frank et al. | 433/169 |

FOREIGN PATENT DOCUMENTS 2237598  2/1974  Fed. Rep. of Germany ...... 433/176

Primary Examiner—John J. Wilson
Attorney, Agent, or Firm—Shook, Hardy & Bacon

[57] ABSTRACT

A device for use in attaching artificial teeth to the bone which supports the natural teeth. The device may have an anchoring member comprising a tooth support receiving member, at least one arm extending laterally from the member, means for coupling the arm with the bone and a spike adapted to be lodged into the bone and extending outwardly from the receiving member. In addition to an anchoring member, the device may comprise a tooth support adapted to be removably positioned upon the anchoring member and designed to allow for limited movement of the artificial teeth.

14 Claims, 2 Drawing Sheets

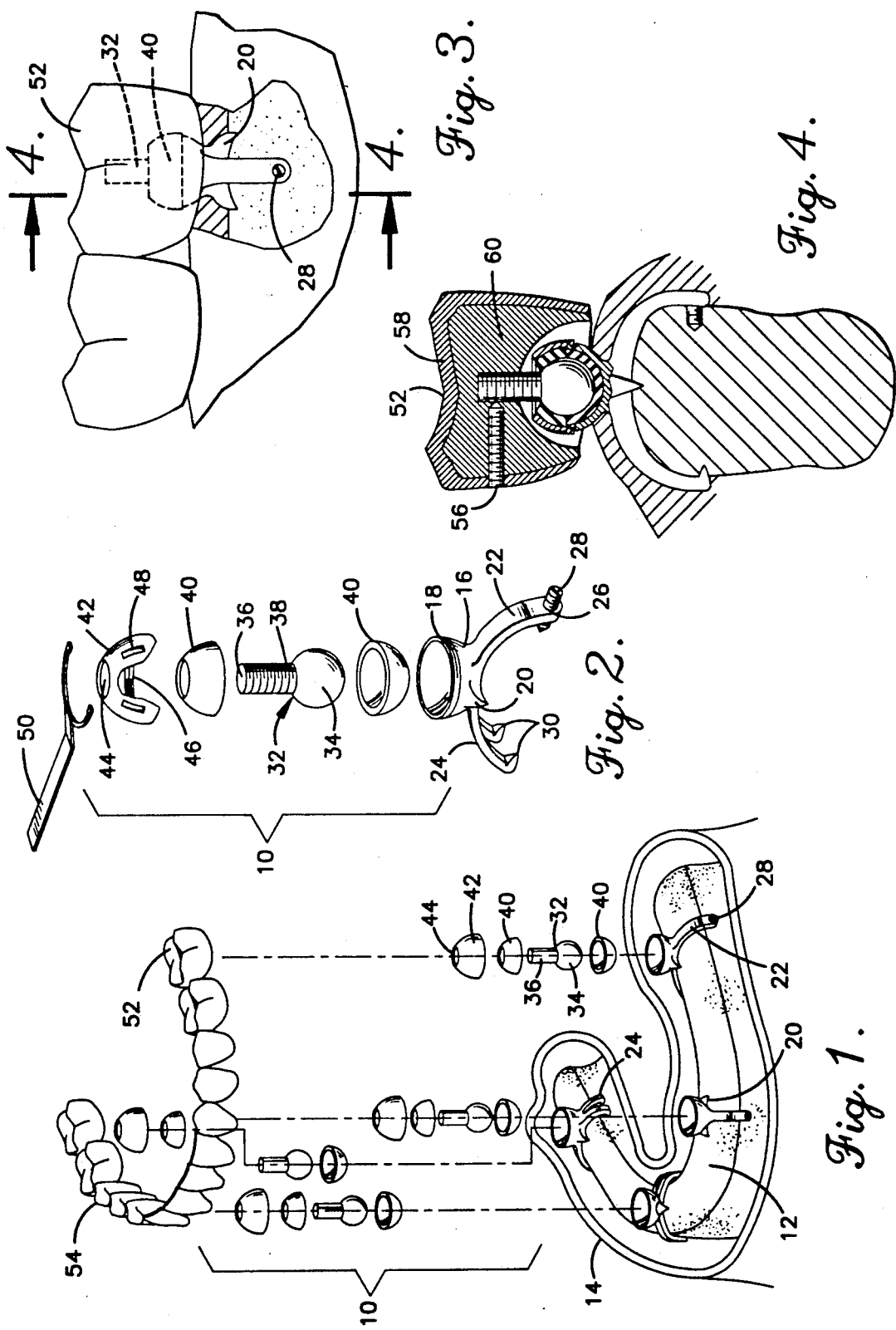

TOOTH IMPLANT DEVICE

FIELD OF THE INVENTION

The present invention pertains in general to the field of dentistry, and more particularly, to a tooth implant device for replacing the natural teeth. Moreover, this invention relates to anchoring artificial teeth to the bone in the mouth and providing for limited movement of the replacement teeth.

DESCRIPTION OF THE RELATED ART

An important aspect of an individual's overall physical health is good oral hygiene. When a tooth becomes damaged or diseased, it is imperative that the problem be remedied. Severely damaged or diseased teeth are often removed completely and replaced by an imitation dental structure such as dentures, an implant or a bridge.

As can be appreciated, great care must be taken when implanting replacement teeth, but the replacement dental work must be capable of being done in a timely manner. Unless a missing tooth is replaced quickly, the remaining teeth shift so that the upper teeth no longer fit properly onto the lower teeth, and plaque builds up more easily, which will increase the likelihood of tooth decay, gum disease and, eventually, further tooth loss.

The most commonly used method of installing a replacement dental structure is to implant a metal peg into the bone. First, the gums are cut open and peeled back. Next, a hole is drilled vertically into the bone in order to receive the metal peg. The peg may have threads, or it may simply be a metal post surgically set into the jawbone. Then, the gums are sewn back together around the protruding peg. Finally, an artificial tooth or crown is glued onto the metal peg.

However, the metal peg implant has several drawbacks. First, its rigid structure does not allow for the natural movement or "give" characteristic of natural teeth. Thus, because there is no "give," an artificial tooth positioned conventionally upon a metal peg implant is prone to shatter if impacted with sufficient force at the right angle by an opposing tooth or some other object.

Second, the metal peg is implanted deep into the narrow ridge of the jawbone. This tends to weaken the bone considerably, and this weakened bone must support the weight of the artificial tooth as well as any forces placed upon it.

Third, the peg implant is not conducive to minor adjustments during installation. For example, if a peg is screwed into or set within the bone at an undesirable angle, it will be difficult to correct that angle. Likewise, if the peg is implanted slightly out of alignment, it may not be feasible to correctly reposition the peg in close proximity without destroying a large portion of the jawbone.

Fourth, this process of installing a metal peg implant usually takes at least three to nine months.

A more recent method of implanting a replacement dental structure involves the use of a full-mouth saddle that rests upon the bone. Here, the saddle must strictly conform to the size and shape of the bone. Consequently, the gums must be opened a first time to take an impression of the patient's bone. The gums must be reopened a second time in order to install this tailor-made saddle. Finally, the gums are reattached in order to hold the saddle in place.

The saddle implant device has several drawbacks as well. First, the gums must be opened on two separate occasions. Second, a saddle must be individually prepared, thus leaving the patient without dentures for months. Finally, the saddle is not actually attached to the bone, so it may not provide adequate support for the artificial teeth.

As can be seen, the devices currently employed in implanting a replacement dental structure either weaken the bone and prohibit the "give" of natural teeth, or else they require at least two operations performed at remote time intervals and provide only minimal support.

Furthermore, when either the metal peg or full-mouth saddle is used to implant dentures, there may be extreme consequences for the patient. These conventional devices do not always stimulate the bone or the gums like the natural teeth do. Consequently, both the bone and the gums may shrink back or recede, and gum diseases are likely to develop. Further, patients are usually forced to restrict their diets due to the structural limitations of the conventional devices.

SUMMARY OF THE INVENTION

It is therefore a primary object of the present invention to provide a device for allowing the artificial teeth the limited movement or "give" that is characteristic of natural teeth.

It is a further object of the present invention to provide an implant device which requires opening the gums only one time.

It is another object of this invention to provide an implant device which does not significantly weaken the jawbone.

It is still another object of the present invention to provide a device which is adjustable during installation and that can be repositioned to correct minor misalignments immediately following initial attachment.

It is another aim of the present invention to provide a device which stimulates both the bone and the gums in a manner closely simulating natural teeth to prevent deterioration of bone and gum tissue.

It is still another aim of the present invention to provide a denture device which allows greater freedom in the patient's diet than conventional dentures allow.

These and other objects may further be achieved by a device comprising a tooth support removably positioned on a tooth anchoring member, which comprises a receiving member, a spike and one or more laterally extending arms. This device can be used advantageously to allow for artificial tooth movement commensurate with that of the natural teeth. Use o this device may help to prevent unnecessary damage to artificial teeth due to impact with an opposing tooth or any other object. The brunt of such an impact may be alleviated dramatically even if the artificial tooth will "give" only a fraction of a millimeter. Also, this device does not significantly weaken the jawbone because it only slightly penetrates the surface of the bone. Further, the present invention requires opening the gums only one time.

Other and further objects of the present invention will become apparent from the following description of the invention and of the accompanying drawings.

BRIEF DESCRIPTION OF THE DRAWINGS

In the accompanying drawings which form a part of the specification and are to be read in conjunction therewith and in which like reference numerals are used to indicate like parts in the various views:

FIG. 1 is an exploded perspective view of the tooth implant assembly of the present invention within the mouth.

FIG. 2 is an exploded perspective view of the tooth implant assembly.

FIG. 3 is a fragmentary side elevational view of the device of the present invention with portions broken away.

FIG. 4 is a cross-sectional view of the device of FIG. 3 taken at line 4—4.

DESCRIPTION OF PREFERRED EMBODIMENTS

Figure 7:
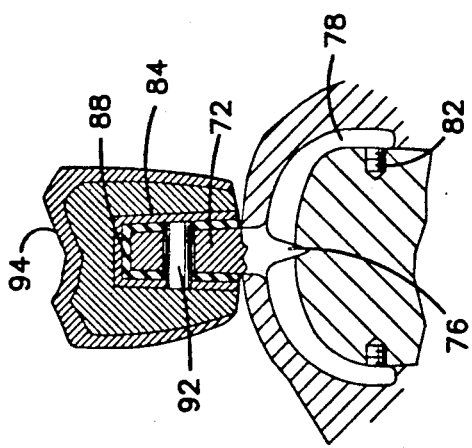
FIG. 7 is a cross-sectional view of the embodiment of FIG. 6.

Referring row to the drawings in greater detail and initially to FIGS. 1 and 2, a tooth implant assembly 10 is designed to rest on jawbone 12 after opening the gums 14. A bowl-shaped tooth support receiving member 16, having a threaded peripheral lip 18, rests on the ridge of bone 12 and is secured in the desired position by spikes 20 and laterally extending arms 22 and 24 which extend on either side of the bone. The spikes 20 flank arms 22 and 24 and are adapted to slightly penetrate the ridge of the bone.

Laterally extending arm 22 presents an aperture 26 at one end which is suitable for threading screw 28 into the front of the bone. Arms 24, on the other hand, have a distal hook end 30 designed to engage the back side of the jawbone.

In FIG. 2, the tooth support 32 includes a spherical base 34 and an integral stem or post 36 with threads 38. Yieldable inserts 40 surround the convex base 34 in order to accommodate limited movement of tooth support 32 when it is received in member 16. A hemispherical collar 42 having a surface opening 44 and peripheral threads 46 is adapted to be threadable received on lip 18 of receiving member 16.

FIG. 2 further details the process of attaching collar 42 to receiving member 16. To facilitate this attachment, collar 42 is lowered over stem portion 36 until it rests upon spherical base 34 and collar threads 46 engage the mating threads on lip 18. Several indentations or notches 48 are arranged about the outer surface of collar 42 so that wrench 50 may "grip" collar 42 and tighten the threads that fasten it to member 16.

Referring now to FIG. 4, artificial tooth 52 is positioned upon tooth support 32 by threading post 36 into the mating threads of tooth 52 either as a single tooth replacement or as one of several anchors for a porcelain bridge 54. Once tooth 52 is in position, set screw 56 penetrates the porcelain coating 58 and the metal crown 60 of artificial tooth 52 in order to engage the threads 38 of tooth support 32.

In application and use, tooth implant assembly 10 will commonly be used to install a set of dentures 54 by implanting four to six devices along the jawbone. Except for yieldable inserts 40, the device may be made from any nonprecious ceramic alloy such as ceradium. However, the device may also be made from any metal or rigid plastic or similar material.

This device is an improvement over related methods of implanting teeth in that installation of it may be completed in one day. First, the gums are opened to reveal the jawbone. Then, a device which corresponds to the width of the jawbone at the desired location may be selected from a plurality of such devices which the dentist will ideally keep on hand.

Once an appropriate device is selected, the dentist may rest the device on the bone by drilling a small hole for each spike 20 or by simply hammering spike 20 into the bone. Each tooth implant device has at least one spike extending from each receiving member 16.

At this point the dentist may wish to verify the position of the receiving member 16 relative to the bone 12. If an adjustment is desirable, the device can be easily removed by withdrawing spike 20 from the bone.

Figure 6:
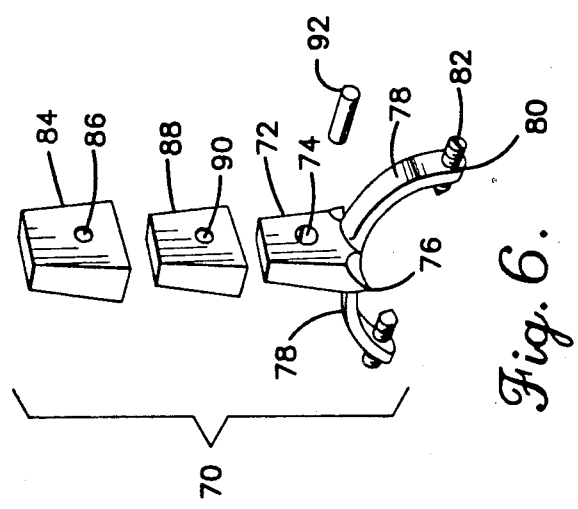
FIG. 6 is an exploded perspective view of another embodiment of the device of this invention.

Next, the device may be further attached to the bone by securing arms 22 or 24 to the bone. For example, arm 22 may present an aperture 26 suitable for threading a screw 28 or other device into the bone as shown in FIG. 6, or arm 22 may simply rest along the bone. Alternatively, the device may include arm 24 having a hook end 30 designed to engage the bone as illustrated in FIG. 2. Further, the device may comprise a plurality of arms 22 and 24 utilizing a combination of securing means with the bone. FIG. 4 reveals a device comprising two arms, and each arm includes a separate means of securing the device to the bone.

Again, the dentist may wish to verify the position of the receiving member once the arms are fastened to the bone. Although the device is attached to the bone in a permanent manner, it may still be adjusted without significant damage to the bone. Since the screw or hook end of the arm is relatively small and only penetrates the side of the bone, only nominal damage to the bone will occur. Thus, the device may be easily adjusted as to its angle or position by reattachment at an improved location.

The tooth support receiving member 16 extends outwardly from the jawbone and presents a concave or bowl-shaped surface. Tooth support 32 is positioned on member 16. For a concave member, the tooth support 32 includes a convex portion 34 as well as an integral stem portion 36. The convex portion will rest upon concave member 16, while the stem portion will receive the artificial tooth. Alternatively, a similar configuration might comprise a convex member receiving a concave portion of tooth support 32. In any case, the tooth support is adapted to be easily positioned upon the member and easily removed as well.

Tooth implant assembly 10 may include at least one yieldable insert 40. The inserts are made of any resilient material such as Teflon (registered trademark of E. I. DuPont de Nemours and Company of Wilmington, Del.) or rubber. In FIG. 1, for example, there are two inserts, one positioned between member 16 and support 32, and the other placed between support 32 and collar 42. As illustrated in FIG. 6, insert 40 is essentially the shape of the surface on which it is to be placed. Additionally, insert 40 may be easily conformed into many shapes and into a variety of positions within assembly 10. It is also within the contemplation of the present invention to provide two or more inserts in one location, such as between member 16 and support 32.

Collar 42 has threads 46 that mate with the threads on lip 18 of receiving member 16 by lowering collar 42 over the stem portion of tooth support 32. Thus, by tightening these mating threads, tooth support 32 will remain substantially stationary, tut is able to pivot in response to forces placed on it. In order to facilitate tightening of the threads, collar 42 may have one or more notches 48 spaced about its circumference. For convenience in "gripping" collar 42 with wrench 50, four notches 48 may be spaced at ninety degree intervals around collar 42. However, any number of notches 48 may be provided within the scope of the present invention.

Figure 5:
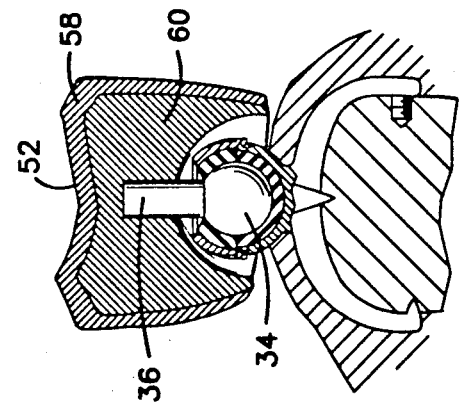
FIG. 5 is a cross-sectional view of another embodiment of the tooth implant device of the present invention.

Once collar 42 has been fastened to member 16, artificial tooth 52 is mounted upon tooth support 32. Tooth 52 may be mounted several ways including the use of adhesives between the stem of tooth support 32 and tooth 52. Such a method of mounting is pictured in FIG. 5. It is preferred, however, that the stem portion of tooth support 32 and the interior of tooth 52 have mating threads as in FIG. 4. When equipped with threads, tooth 52 will also present an aperture through porcelain coating 58 and metal crown 60, so that set screw 56 will engage the threads on the stem portion. Thus, set screw 56 will prevent tooth 52 from unscrewing due to vibration or other causes.

FIGS. 6 and 7 illustrate tooth implant assembly 70, another embodiment of the tooth implant device. Implant assembly 70, like assembly 10, is designed to rest on the jawbone after surgically opening the gums. A vertically protruding receiving member 72, having an aperture 74, rests on the ridge of the bone and is secured in the desired position by spikes 76 and laterally extending arms 78 which extend on either side of the bone.

Arms 78, similar to arm 22 of assembly 10, present an aperture 80 suitable for threading screw 82 into either side of the bone, although arm 78 could also have a hook end.

Aperture 74 through member 72 is adapted to receive a cylindrical movement pin 92. As shown in FIG. 7, pin 92 penetrates receiving member 72.

FIG. 6 shows that tooth support 84 corresponding to vertically protruding member 72 is substantially U-shaped in cross-section. Accordingly, tooth support 84 is adapted to be easily positioned upon member 72 and easily removed as well. Further, one side of tooth support 84 presents an aperture 86 adapted to receive movement pin 92.

Yieldable insert 88 is also substantially U-shaped in cross-section and is positioned between member 72 and tooth support 84. Insert 88 presents an aperture 90 corresponding to aperture 86 of tooth support 84.

In application and use, the embodiment of FIG. 6 provides for limited movement of an artificial tooth 94 by inserting a movement pin 92 through aperture 86 in tooth support 84, aperture 90 in yieldable insert 88 and aperture 74 in receiving member 72. As shown in FIG. 7, pin 92 completely penetrates member 72, but passes through only one side of tooth support 84. Pin 92 allows for limited movement since the aperture 74 through member 72 is larger in diameter than the aperture 86 in the side of tooth support 84. After inserting pin 92, artificial tooth 94 is mounted upon tooth support 84 as in FIG. 7.

Tooth implant assembly 70 allows for less movement than assembly 10. Accordingly, assembly 70 is better suited for implanting individual artificial teeth, but it is feasible to use the vertical protruding member for dentures.

Figure 9:
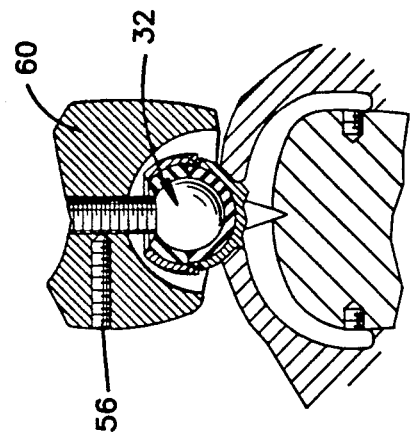
FIG. 9 is another cross-sectional view of the embodiment of FIG. 8 without the protruding stem.
Figure 8:
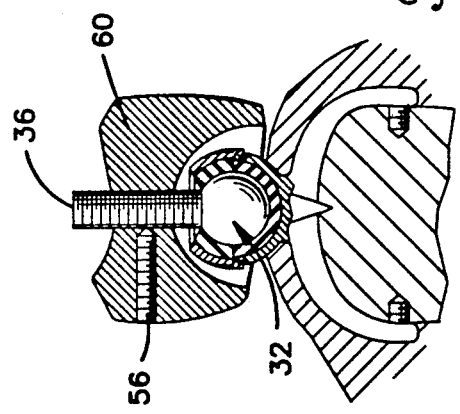
FIG. 8 is a cross-sectional view of yet another embodiment of the device of the present invention.

FIGS. 8 and 9 depict yet another embodiment of the tooth implant device in which there is n porcelain coating upon metal crown 60.

In certain situations, there is not enough room for a standard artificial tooth. Thus, metal crown 60 is installed on tooth support 32 in place of artificial tooth 52. Valuable space is conserved by providing a metal crown 60 without porcelain coating 58. When metal crown 60 is fastened to a desired height on tooth support 32 using mating threads, the stem portion 36 of the tooth support may extend beyond the top of crown 60 as in FIG. 8. The dentist may shave off this excess stem portion, as in FIG. 9, so that it is flush with crown 60.

All embodiments of the tooth implant device may be used to install single implants or complete dentures. However, considering the amount of movement allowed by the various embodiments, it is advisable to use the concave member for installing dentures or multiple artificial teeth. Conversely, the vertically protruding member is better suited for single tooth implants.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without department from the scope thereof, it is to be understood that all matter herein set forth or shown in the accompanying drawings is to be interpreted as illustrative and not in a limiting sense.

Having thus described the invention, I claim:

1. A tooth implant device for attachment to the bone which supports the natural teeth, said device comprising:

a tooth support receiving member adapted to be positioned on said bone and extend outwardly from the ridge of the bone, said receiving member having an outwardly concave surface constructed for receiving a convex base portion of a tooth support;

at least one arm extending in a lateral direction from said member and adjacent at least one side of said bone;

means for securing said arm to said bone; and a spike extending outwardly from said member and adapted to be lodged into said bone.

2. The device of claim 1, wherein said arm presents an aperture adapted to accommodate said securing means.

3. The device of claim 1, including a tooth support removably positioned on said member and having a spherical base and a post extending outwardly from said base.

4. The device of claim 3, further comprising a yieldable surface positioned between said receiving member and said tooth support base.

5. The device of claim 3, further comprising an artificial tooth positioned upon said tooth support post.

6. The device of claim 5, wherein said tooth and said tooth support present mating threads.

7. The device of claim 3, further comprising a collar received by said stem portion for coupling said tooth support with said receiving member.

8. The device of claim 7, including threads on said receiving member adapted to be mated with corresponding threads on said collar.

9. The device of claim 7, further comprising a yieldable surface positioned between said tooth support and said collar.

10. A tooth implant device for attachment to the bone which supports the natural teeth, said device comprising:
- a tooth support receiving member constructed for positioning on said bone and having a concave surface positioned for extending outwardly from a ridge of the bone;
- a arm extending in a lateral direction from said receiving member for placement adjacent at least one side of said bone;
- a spike extending from said member and positioned to be lodged into said bone;
- a tooth support comprising a base and a post extending outwardly from said base for receiving an artificial tooth, said base having a convex portion size for being received by the concave surface of said receiving member to permit tilting movement of said post; and
- a collar for coupling said tooth support with said receiving member.

11. The device of claim 10, including threads on said receiving member for mating with corresponding threads on said collar.

12. The device of claim 11, including a yieldable surface position between said receiving member and said base of the tooth support.

13. The device of claim 12, including a yieldable surface position between said base of the tooth support and said collar.

14. The device of claim 13, including an artificial tooth positioned upon said post of the tooth support.

* * * * *